United States Patent [19]
Wadler

[11] Patent Number: 5,814,640
[45] Date of Patent: Sep. 29, 1998

[54] METHOD OF TREATING GASTROINTESTINAL MALIGNANCIES

[75] Inventor: Scott Wadler, Larchmont, N.Y.

[73] Assignee: Montefiore Medical Center, Bronx, N.Y.

[21] Appl. No.: 831,925

[22] Filed: Apr. 2, 1997

Related U.S. Application Data

[63] Continuation of Ser. No. 317,377, Oct. 4, 1994, abandoned.

[51] Int. Cl.[6] .......................... A61K 31/505; A61K 38/21
[52] U.S. Cl. ............................................ 514/274; 424/85.6
[58] Field of Search ............................. 514/274; 424/85.6

[56] References Cited

PUBLICATIONS

Lillis et al, Cancer Treat Rep (Oct. 1987) 71(10) pp. 965–7–(Abstract only).

*Primary Examiner*—Jerome D. Goldberg
*Attorney, Agent, or Firm*—Hedman, Gibson & Costigan, P.C.

[57] ABSTRACT

The present invention provides a method for the treatment of carcinoma. Those carcinomas include those of visceral origin and in particular gastrointestinal malignancies. The method comprises administering an amount of 5-fluorouracil and an amount of interferon which is effective in the palliation of said carcinoma or malignancy. Alpha, beta or gamma interferon may be used but recombinant alpha-2a-interferon is preferred.

3 Claims, 5 Drawing Sheets

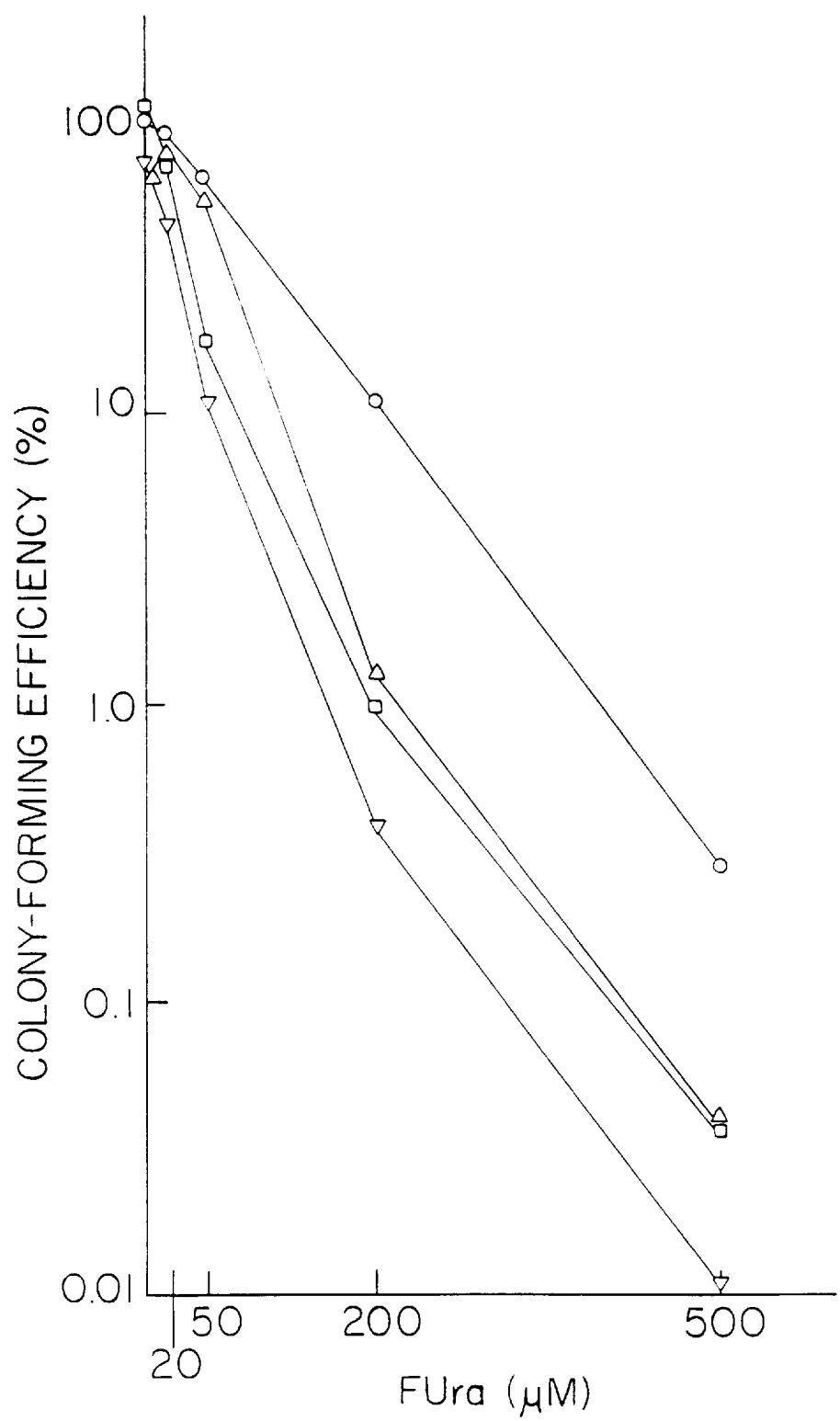
FIG. 1-A

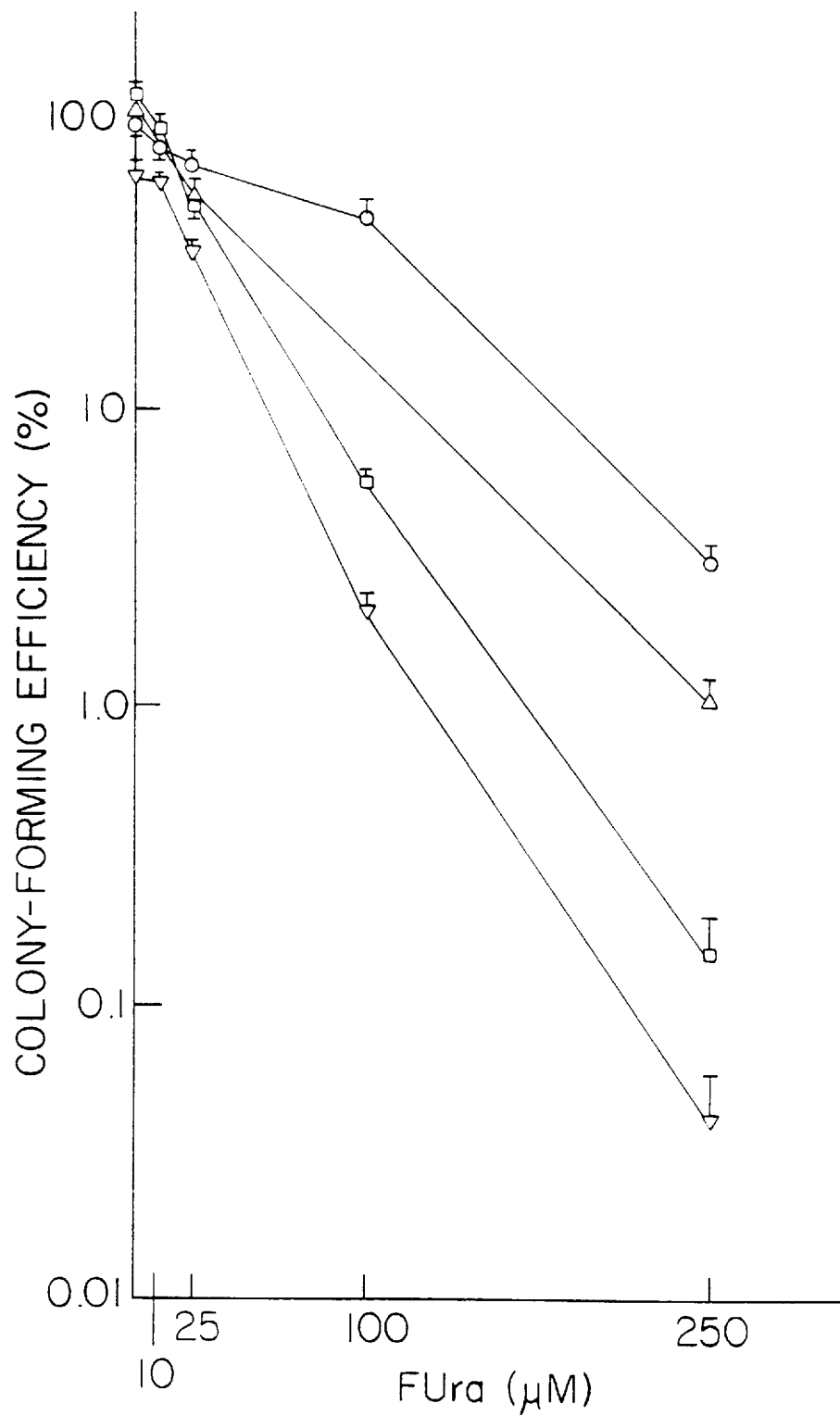
FIG. 1-B

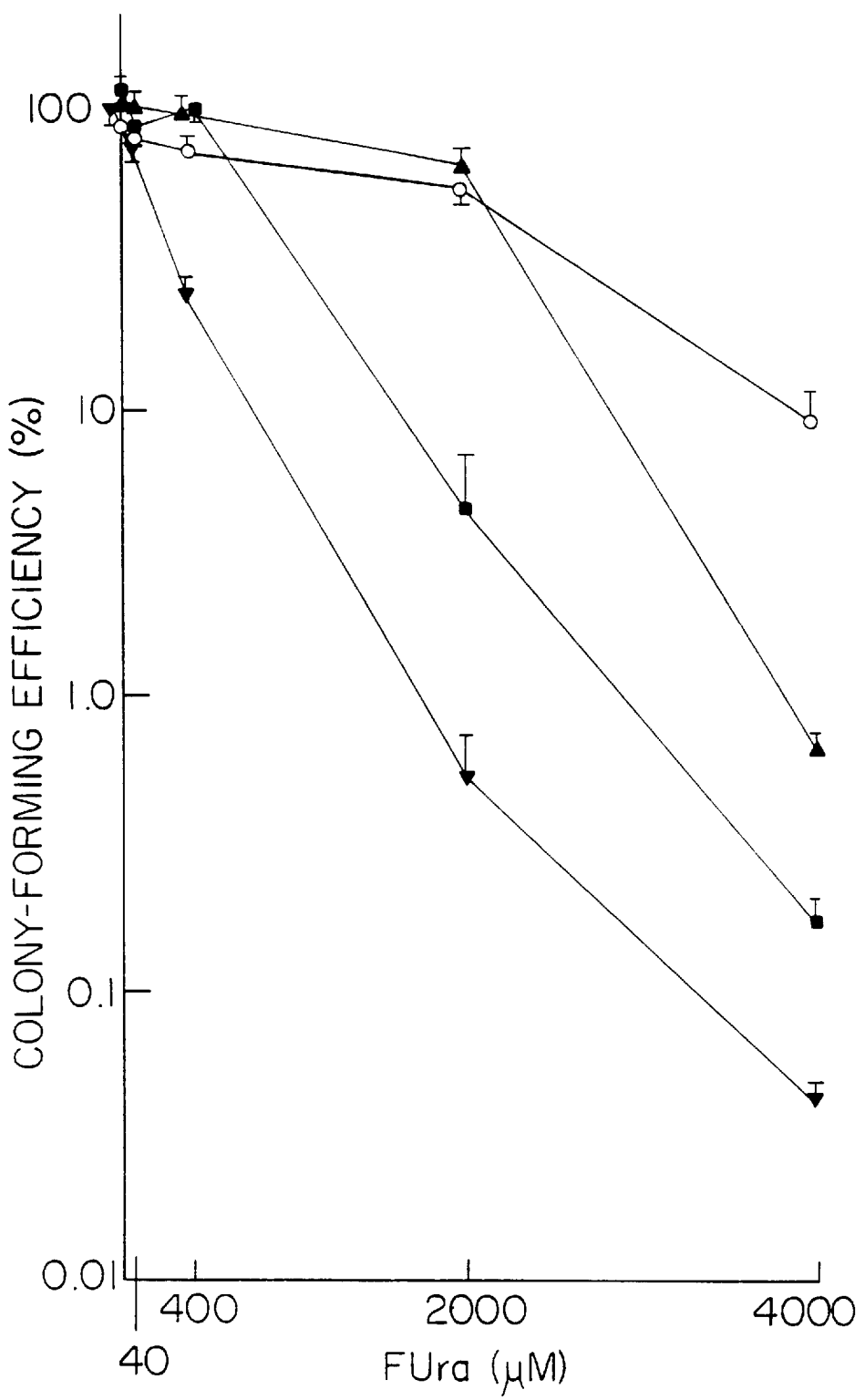
FIG. 1-C

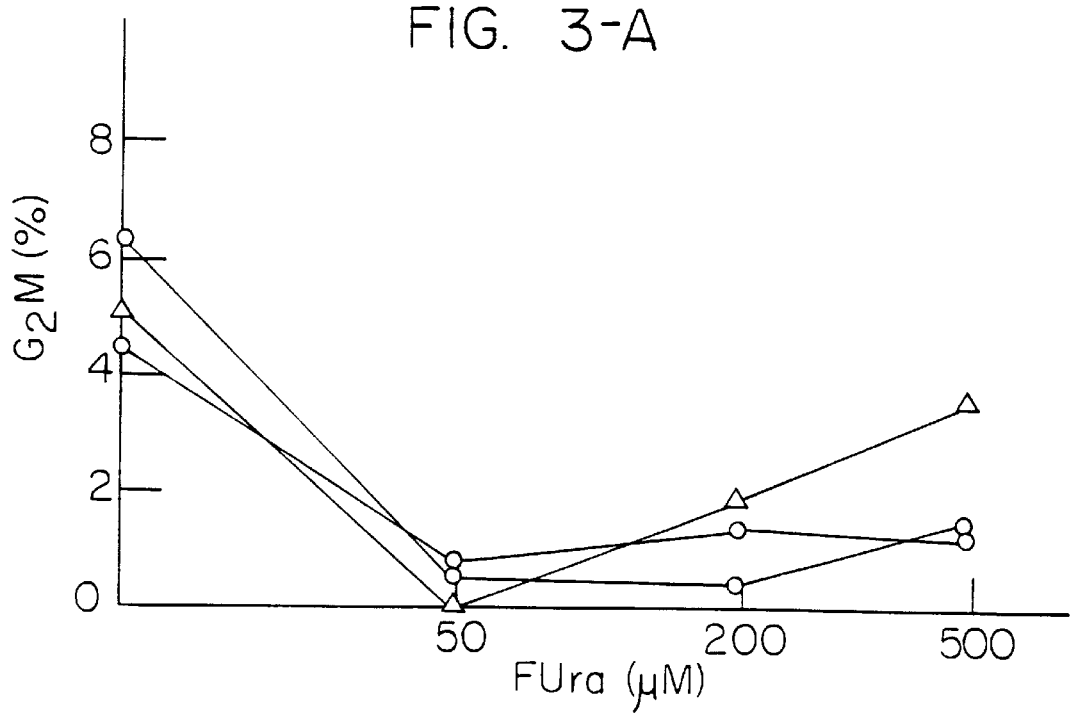
FIG. 3-A
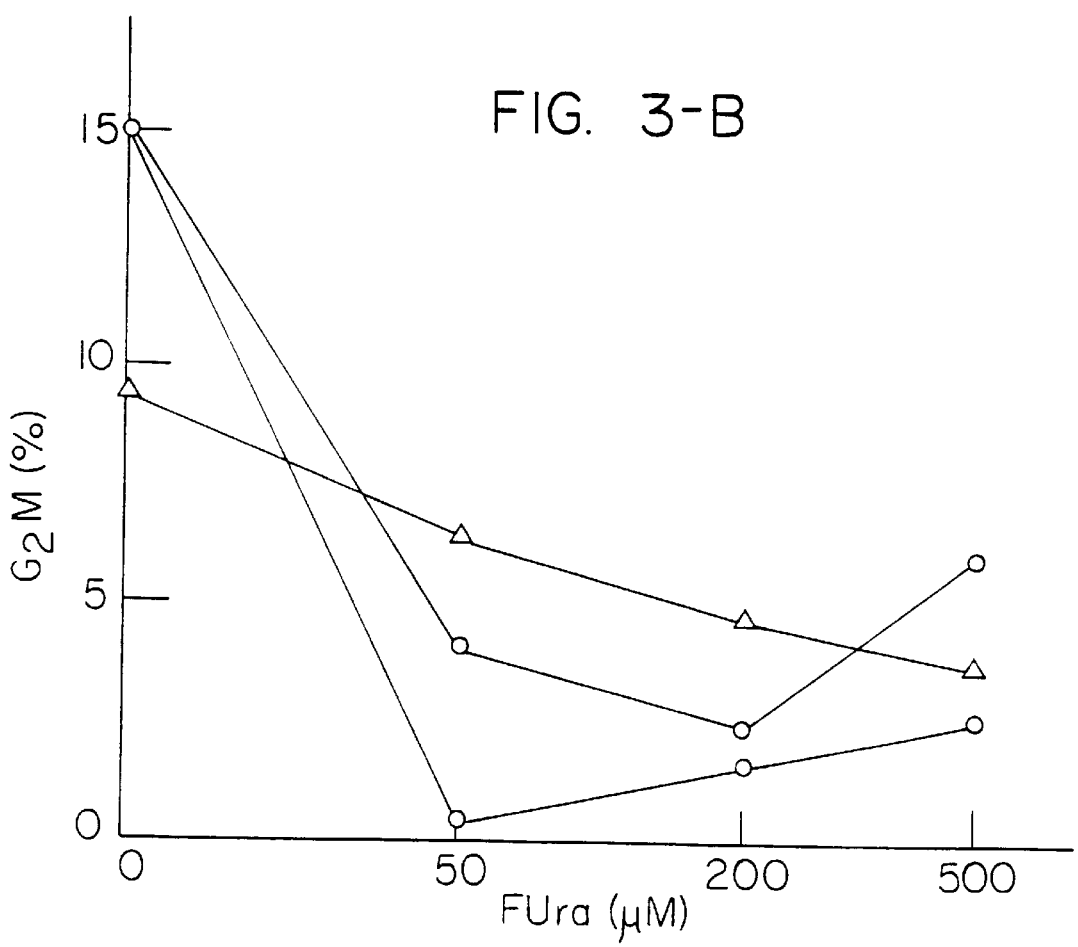
FIG. 3-B

METHOD OF TREATING GASTROINTESTINAL MALIGNANCIES

This is a continuation, of application Ser. No. 08/317,377, filed Oct. 4, 1994 now abandoned.

BACKGROUND OF THE INVENTION

This invention provides a novel method for the treatment of gastrointestinal malignancies.

Patients with advanced unresectable colorectal carcinoma have a uniformly poor prognosis. In addition to the significant mortality from this disease, patients often experience severe morbidities including obstruction of the gastrointestinal tract, liver failure, massive ascites, cachexia and inanition.

The compound, 5-fluorouracil, is the principal chemotherapeutic agent which is employed against colorectal cancer even though it induces remissions in only 15–35% of patients with disseminated colorectal cancer. The patients who do respond rarely respond completely and the duration of the response is generally short. The median survival of treated patients is no better than that of untreated controls.

The failure of conventional chemotherapy to provide durable, disease - free remissions against gastrointestinal malignancies has prompted research aimed at developing alternative treatments which are more effective than 5-fluorouracil employed alone. One approach to enhancing the effect of 5-fluorouracil has been the concomitant use of agents which by themselves have little or no activity against refractory solid tumors, but which in combination modify the metabolism or disposition of 5-fluorouracil to amplify its anti-tumor activity.

The applicant has discovered that the use of 5-fluorouracil in a systematic dosage regimen with concomitant administration of interferon will provide a more effective chemotherapeutic approach to the treatment of gastrointestinal malignancies than the use of either drug alone. The applicant has confirmed the efficacy of the novel method of the invention by studies in human cancer cell lines and in clinical experiments. These results are surprising and unexpected in view of the lack of prior success with combinations of 5-fluorouracil and interferon which were probably due to the use of an inadequate dosage and offers the first demonstration of the enhancement by interferon of the activity of any chemotherapeutic agent against a refractory solid tumor.

BRIEF DESCRIPTION OF THE DRAWINGS

FIG. 1 is a series of graphs which shows the cloning efficacy of the HT-29 and SW-480 cell lines in the presence or absence of 5-fluorouracil and/or alpha-2a-interferon.

FIG. 3 shows the cytokinetic effects against the HT-29 and SW-480 cell lines of 5-fluorouracil and alpha2a-interferon when used alone or in combination at increasing doses.

SUMMARY OF THE INVENTION

Figure 2:
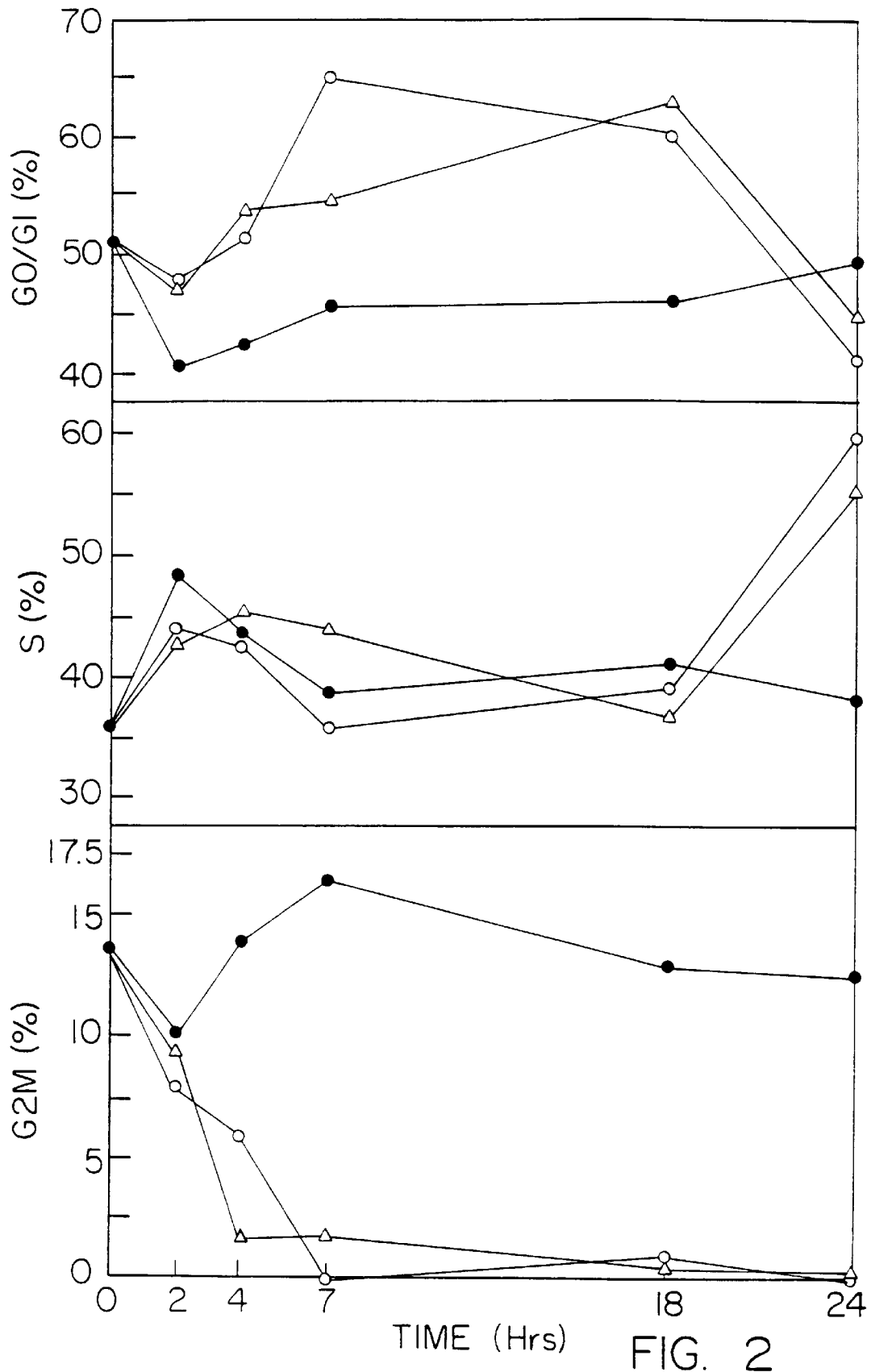
FIG. 2 shows the effect of cytokinetic studies with or without 5-fluorouracil and alpha-2a-interferon when used alone or in combination against the HT-29 cell line for varying durations.

The present invention provides a method for the treatment of carcinoma. Those carcinomas include those of visceral origin and in particular gastrointestinal malignancies. The method comprises administering an amount of 5-fluorouracil and an amount of interferon which is effective in the palliation of said carcinoma or malignancy. Alpha, beta or gamma interferon may be used but recombinant alpha-2a-interferon is preferred. The method of the invention may be used to treat various malignancies including esophogeal carcinoma, stomach carcinoma, pancreatic carcinoma, liver carcinoma, small bowel carcinoma, biliary carcinoma, adenocarcinoma of unknown primary, carcinoid tumor and colorectal carcinoma.

DETAILED DESCRIPTION OF THE INVENTION

The method of the invention is based on the administration of 600–1000 $mg/m^2$/day of 5-fluorouracil followed by the administration of from 2–40 million international units of alpha-2a-interferon. The 5-fluorouracil may be administered parenterally, preferably intravenously in divided doses or continuously. The daily dose is repeated for 4–10 days followed by 4–10 days of rest before commencing another sequence of 5-fluorouracil therapy. The subsequent 5-fluorouracil administration may be in 4–10 day sequences or once every 4–10 days, preferably about every 7 days as a bolus intravenous injection of 600 $mg/m^2$ to 1000 $mg/m^2$, preferably 750 $mg/m^2$.

A preferred dosage regimen is about 750 $mg/m^2$ day of 5-fluorouracil for about 5 days followed by a one week rest period along with 2–40 million international units of recombinant alpha-2a-interferon/day subcutaneously, 3–7 times a week. A preferred dose for alpha-2a-interferon is about 9 million international units per day 3–7 times a week, preferably about 3 times a week. The course of therapy may be carried out for a period of 2–52 weeks. Depending on the therapeutic response and the manifestation of unacceptable toxic side effects, the dose may be increased or decreased within the general description set forth herein.

The activity of the combination of 5-fluorouracil and alpha-2a-interferon against a human colon cancer cell line was confirmed by testing the combined agents on the colon cancer cell lines HT-29 and SW480 (Fogh J, Trempe G. New Human Tumor Cell Lines. In: Fogh J, ed *Human Tumor Cells In Vitro*. New York: Plenum Press (1975) pp. 115–159). Cells were cultured in RPMI 1640 with 10% fetal calf serum. Doubling times for these cell lines are 18 and 25 hours.

A clonogenic assay was carried out by trypsinizing HT-29 and SW480 cells, washing the cells twice with phosphate buffered saline (PBS), resuspending in RPMI 1640 with 10% fetal calf serum, and adjusting the cell concentration to 400–4000 cells/ml. Cells were plated in plastic Petri dishes, and exposed to the drug on day 2–3, during exponential growth. At 2–72 hours, the cells were washed with PBS three times and incubated for 14–18 days. Cells were fixed and stained with Coomassie Blue in a one-step process, then counted under low power magnification. A colony comprised at least 33 cells. Cloning efficiency was 63% for HT-29 and 16% for SW480. All experiments were performed in triplicate. Differences were compared by analysis of variance. As shown in FIG. 1a and 1b, simultaneous 24 hour incubation with alpha-2a-interferon and 5-fluorouracil resulted in greater cell kill in both HT-29 and SW480 cell cultures than incubation with 5-fluorouracil alone at all three dose levels of alpha-2a-interferon tested. Higher concentrations of alpha-2a-interferon resulted in greater modulation of the 5-fluorouracil effect. This was not merely an additive effect as incubation with alpha-2a-interferon alone resulted in less than 40% cell kill. When cells were incubated with 5-fluorouracil for 2 hours, the lethality of 5-fluorouracil was also enhanced, but the magnitude of the effect was not as great as with simultaneous 24 hour incubation with both drugs (data not shown).

The length of exposure to alpha-2a-interferon was a critical determinate of cell kill in the presence of 5-fluorouracil (FIG. 1c). In HT-29 cell cultures incubation with alpha-2a-interferon for 24 hours following 2 hour exposure to 5-fluorouracil resulted in enhanced cell kill only at the highest concentrations of 5-fluorouracil employed, whereas 48 and 72 hour incubations with alpha-2a-interferon enhanced 5-fluorouracil effects at lower concentrations as well. When HT-29 cells were incubated with alpha-2a-interferon and 5-fluorouracil for only 2 hours, there was no enhancement of the 5-fluorouracil effect.

The sequence of exposure to drug was also an important determinate of drug effect, although only in the HT-29 cell cultures. When cells were exposed to alpha-2a-interferon for 24 hours prior to 2 hour 5-fluorouracil incubation, the cytotoxic effects of the latter drug were almost completely abrogated. In the SW480 cell cultures, the sequence alpha-2a-interferon/5-fluorouracil was as effective as 5-fluorouracil/alpha-2a-interferon.

Cytokinetic studies were carried out to determine the effect of the combination of 5-fluorouracil and alpha-2a-interferon on cell cycle progression of HT-29 and SW480 cells. The DNA content of propidium-iodide stained nuclei was measured by flow cytometry. Cells in early exponential growth were incubated with or without drug, trypsinized and washed twice in PBS. A total of $10^6$ viable cells, as determined by trypan blue exclusion, were permeabilized in sucrose-citrate-DMSO buffer as described by Vindelov et al., enucleated with trypsin and incubated with RNAse. Stripped nuclei were stained with propidium iodide at a final concentration of 2.5 ug/ml. Correlated dual parameter measurements of DNA content (from propidium-iodide red fluorescence excited at 488 nm) versus forward angle light scatter were performed using an EPICS C flow cytometer equipped with a 5W ultraviolet enhanced argon ion laser. Histograms consisting of a minimum of 10,000 nuclei were analyzed off-line with an EPICS C to RSX-11M conversion program (EPICOPY) and subsequently analyzed with ROMP and ROC3D programs rewritten for a DEC 11/73 computer. Cell cycle analysis for the compartmental boundaries and number of cells in the G1, S, and G2M phases was performed on ROMP-readable files using either a multiple gaussian fitting routine developed by Dean et al. or, for the perturbed histograms, a parametric method based on multiple broadened rectangles. The coefficient of variation of the G0/G1 peak of PI-stained lymphocyte controls was 1.8–2.1%.

The most important effect on cell cycle distribution resulting from incubation with 5-fluorouracil and alpha-2a-interferon for 24 hours was nearly complete depletion of the G2M compartment. Time course studies revealed that this effect occurred within 7 hours of start of incubation and occurred following incubation with 5-fluorouracil alone. The effect on G2M was accompanied by an increase in the number of cells in S phase within 2 hours, which must have resulted from partial block of the transition from S to G2M. The largest increase during the first 7 hours of treatment was in G0/G1 suggesting that the cells leaving G2M entered G0/G1 and were delayed from further progression. This block was reversed by 18 hours, such that the percentage of cells in G0/G1 decreased. At 24 hours, the predominant cytokinetic effect was accumulation of cells in S phase.

Incubation with alpha-2a-interferon alone had only minimal effects on cell cycle distribution with the predominant effect being a transient block in S phase at 2 hours which almost completely reversed by 7 hours. The effect of the combination of 5-fluorouracil and alpha-2a-interferon on cell cycle traverse was nearly identical to that of 5-fluorouracil alone. Incubation of SW480 cells with 5-fluorouracil and alpha-2a-interferon alone or in combination resulted in qualitatively identical effects with the sole exception of a prolongation of the block in G0/G1 to 24 hours and a concomitant decrease in the accumulation of cells in S and G2M at 24 hours (data not shown).

FIGURE LEGENDS

FIG. 1 - Cloning efficiency of HT-29 (A) and SW480 (B) cell cultures following 24 hour incubation with 5-fluorouracil in the absence (○) or presence of alpha-2a-interferon, 50 (△), 500 (□), or 5000 (▽) U/ml. (C) Cloning efficiency of HT-29 cells following 2 hour incubation with 5-fluorouracil alone (○) or followed by alpha-2a-interferon, 500 U/ml, for 24 (▲), 48 (■), or 72 (▼) hrs. Points: mean of 3 experiments. Bars: standard error of the mean. For la standard error bars lie within or on points. In 1b, one data point is unavailable. There is a significant interaction between 5-fluorouracil and alpha-2a-interferon, and an overall significant linear effect associated with change in alpha-2a-interferon dose by two-factor analysis of variance (P .01).

FIG. 2 graphically shows time course studies of the effects of incubation with alpha-2a-interferon 500 U/ml (●), 5-fluorouracil, 50 uM (○), or the combination (△) on the cell cycle distribution of HT-29 cells. Cell population were incubated with drug(s) for varying time periods, then prepared as described hereinabove. The abscissa represents the number of hours cell populations were exposed to drug.

The ordinate represents the percentage of total cell population in each cell cycle compartment.

FIG. 3 is a graphical representation of a dose response study of the cytokinetic effects of 5-fluorouracil alone (●) or 5-fluorouracil and alpha-2a-interferon 50 U/ml (○) or 5000 U/ml (△) The abscissa represents the dose of 5-fluorouracil and the ordinate represents the percentage of the total cell population in the G2M compartment following 24 hours of incubation with and without the drug.

The dose response effects of 5-fluorouracil and alpha-2a-interferon on cell cycle distribution were investigated following 24 hour incubation with each drug alone or in combination. As shown in FIG. 3, incubation with 5-fluorouracil at doses from 50–500 uM produced nearly complete depletion of G2M in both HT-29 and SW480 cell cultures. The addition of alpha-2a-interferon at 50 U/ml or 5000 U/ml failed to modulate the effect of 5-fluorouracil in HT-29 cells. In SW480 cell cultures, alpha-2a-interferon partially reversed the depletion of the G2M compartment, probably resulting from generalized inhibition of traverse through all cell cycle phases.

DESCRIPTION OF THE PREFERRED EMBODIMENTS

EXAMPLE

A clinical trial was carried out with combined administration of 5-fluorouracil and alpha-2a-interferon.

The eligibility requirement for patients included histologically-proven metastatic colorectal adenocarcinoma not amenable to surgical resection, bidimensionally measurable disease outside a radiation portal or hepatomegaly if the liver was measurable 5 cm or greater below the costal margin, adequate bone marrow function defined as a white blood cell count 4000/μl and platelet count 100×10³/μl, adequate renal function defined as serum creatinine 2.0 mg/dl, adequate hepatic function defined as serum bilirubin less than three times normal, Eastern Cooperative Oncology Group (ECOG) performance status of 2 or less, recovery from surgery, adequate caloric intake, absence of active infection, and ability to sign informed consent. The informed consent met all institutional and federal guidelines.

The study design employed a loading course of 5-fluorouracil, 750 mg/m² by continuous intravenous infusion daily for five days, followed by one week rest, then weekly bolus therapy. Alpha-2a-interferon, 9 million international units was administered subcutaneously three times weekly starting day one. Patients received acetaminophen, 650 mg. orally one-half hour prior to receiving alpha-2a-interferon, then every 4 hours thereafter for 3 doses. Patients were prohibited from receiving steroids or non-steroidal antiinflammatory agents. The dose of 5-fluorouracil was modified for stomatitis, diarrhea, and myelosuppression; the dose of alpha-2a-interferon for cerebral, hepatic, or renal toxicity as well as worsening of performance status thought secondary to treatment.

Standard ECOG criteria were employed for evaluating response to therapy. A partial response required 50% reduction in the sum of the products of the perpendiculars of all measurable lesions. If hepatomegaly was the indicator, a 30% reduction of the sum of the liver measurements below the right costal margin at the midclavicular line and xiphoid was required, without worsening of liver function. A complete response required disappearance of all lesions deemed pathological. Thus, persistence of fibrotic changes in the pelvis, even if unmeasurable, precluded complete response unless absence of disease could be verified pathologically. Where response was assessed by radiologic criteria, agreement of both a radiologist and clinician was required. Scans were performed on the Siemen's DRH scanner with a scan time of 4 seconds at 125 Kvp. Key lesions were measured on the physician's viewing console with electronic calipers. Images were photographed on the Siemen's Multispot M camera. End-points of therapy included complete response to therapy, progressive disease or unacceptable toxicity not responding to dose modification.

A total of 27 patients were entered into a clinical trial. Demographic characteristics for the patients in the study are shown in Table 1. All patients were eligible and evaluable for toxicity. Three patients were inevaluable for response. One with a pre-existing seizure disorder suffered a partial complex seizure after the first dose of alpha-2a-interferon and was removed from study. A second developed bronchospastic episodes temporally associated with alpha-2a-interferon treatments and was removed from study. A third patient, discussed below, who by physical examination had achieved a partial response, expired prior to confirmation of response by computed tomographic scan and was thus deemed inevaluable.

As shown in Table 2, among the 12 previously untreated patients evaluable for response a total of 11 achieved an objective response. One patient was a complete responder. All objective responses occurred in visceral organs, either lung or liver, except for one patient responding in the sacrum. Among patients achieving a major response, three had bulky visceral disease including diffuse permeation of the entire liver, complete effacement of one lobe of the liver, or nodular replacement of greater than 50% of the liver with tumor. The median time to response was 6 weeks. One patient who had experienced daily hectic fevers thought secondary to tumor involvement of the liver completely resolved the fevers within one week and had marked reduction in hepatomegaly within two weeks of initiating therapy. Two patients, one with a bone metastasis described above, responded at 3 months. Among the 12 previously untreated patients, only one patient experienced disease progression after initiation of therapy. Duration of response, progression free survival and overall survival for the 12 previously untreated patients are shown in Table 2.

Of 12 previously treated patients evaluable for response, all had received a combination of 5-fluorouracil with either leucovorin or methotrexate. None achieved a major response, although 2 had minor tumor regression and 4 had stable disease.

There were two instances of life-threatening toxicities among the patients enrolled in this trial, both in patients in clinical response. One patient developed the abrupt onset of watery diarrhea followed by leukopenia and fevers which persisted for 36 hours prior to administration of antibiotics. Despite aggressive antibiotic therapy and blood pressure support, the patient became septic and hypotensive, and expired. A second patient also developed diarrhea followed by leukopenia and fevers. Antibiotic therapy and hydration were instituted immediately resulting in clinical improvement. The white blood cell count ecovered from 1000 /ul with 7% granulocytes to 5600/ul, and the patient's fever and azotemia resolved. On the eighth hospital day the patient expired from unexplained causes.

Other toxicities almost always responded to dose reduction. During weekly bolus therapy, dose reductions were employed in over half the patients, usually for fatigue or myelosuppression. Hematologic toxicities associated with administration of this regimen were acceptable with the two exceptions noted above. The absence of cumulative myelosuppression most likely resulted from dose reductions. Anemia was common, but was more likely to result from low-grade gastrointestinal hemorrhage than from treatment. There were no episodes of thrombocytopenic hemorrhage.

Gastrointestinal toxicities were common. Stomatitis tended to occur immediately following the induction course, rarely later, and in two instances was severe. Diarrhea tended to occur later. The presence of diarrhea required temporary discontinuation of therapy. Cerebral toxicity was protean including headache, loss of equilibrium, and emotional lability. One patient experienced a mild expressive aphasia; however, this patient later admitted to abusing alcohol throughout his treatment course.

Toxicities associated with administration of alpha2a-interferon occurred predictably and included fever, chills, and myalgias. Most patients developed tachyphylaxis to these symptoms. Nearly half the patients suffered a transient worsening of performance status by one or two levels while on alpha-2a-interferon, although this was more often associated with tumor progression. Less common side effects of this regimen included hyperpigmentation or erythematous maculopapular rash in five patients, palmar erythema in two, dysgeusia in six, and dacrocystitis in two.

TABLE 1

Demographic Characteristics

| | n |
|---|---|
| Eligible | 27 |
| Evaluable for toxicity | 27 |
| Evaluable for response | 24[a] |

TABLE 1-continued

Demographic Characteristics

|  | n |
|---|---|
| M:F | 17:10 |
| Age (years) | |
| Median | 57 |
| Range | 32–78 |
| Primary Lesion | |
| Colon | 23/27 |
| Rectum | 4/27 |
| Sites of metastatic disease | |
| Liver | 22/27 |
| Lung | 7/27 |
| Lymph nodes | 4/27 |
| Bone | 3/27 |
| Peritoneum | 2/27 |
| Adrenal | 1/27 |
| Prior surgery | 24/27 |
| Prior radiation | 4/27 |
| Prior chemotherapy | 13/27 |
| Methotrexate - FUra | 6/27 |
| Leucovorin - FUra | 6/27 |
| FUra | 1/27 |

[a]3 patients removed from study prematurely (See Text).

TABLE 2

Response and Survival data in 12 previously untreated patients treated with 5-fluorouracil/alpha-2a-interferon.

| Patient | Site | Resp. | Dur (mo) | PFS (mo) | Status | Survival (mo) |
|---|---|---|---|---|---|---|
| 1 | Liver | CR | 3+ | 4+ | NED | 4+ |
| 2 | Liver | PR | 4+ | 6+ | AWD | 6+ |
| 3 | Lung | PR | 6 | 8 | DWD | 12 |
| 4 | Liver, lung | PR | 6 | 8 | AWD | 16+ |
| 5 | Liver | PR | 2 | 4 | DWD | 6 |
| 6 | Liver, lung | PR | 3+ | 5+ | AWD | 5+ |
| 7 | Bone | PR | 3+ | 6+ | AWD | 6+ |
| 8 | Lung | PR | 6 | 8 | AWD | 10+ |
| 9 | Lung | PR | 5+ | 7+ | AWD | 7+ |
| 10 | Liver | PR | 3+ | 5+ | AWD | 5+ |
| 11 | Liver, lung | PR | 2+ | 4 | DWD | 4 |
| 12 | Liver | PD | — | — | DWD | 1 |

Abbreviations: Resp, repsonse: Dur, response duration; PFS, progression free survival; AWD, alive with disease; DWD, dead with disease; NED, no evidence of disease; CR, complete response; PR, partial response; PD, progressive disease; mo, month

I claim:

1. A method for the treatment of a malignancy sensitive to a treatment regimen which comprises administering by injection to a host afflicted with said malignancy 5-fluorouracil at a dose of 600–1000 mg/m$^2$/day followed by the administration of from 2–40 million international units of beta interferon 3 to 7 times weekly commencing on the first day that 5-fluorouracil therapy is instituted.

2. A method as defined in claim 1, wherein a dose of about 750 mg/m$^2$/daily of 5-fluorouracil is administered daily for five days by continuous intravenous infusion followed by a one week rest period followed by a once weekly injection of about 750 mg/m$^2$ of 5-fluorouracil along with 2–40 million international units of beta interferon which is administered 3–7 times a week.

3. A method of treating colorectal cancer which comprises first administering to a host afflicted with colorectal cancer about 750 mg/m$^2$/day of 5-fluorouracil for about five days by intravenous infusion followed by a one week rest period, followed by once weekly bolus injections of 5-fluorouracil and administering about 9 million international units of beta interferon subcutaneously about three times weekly concurrent with initiation of the intravenous infusion of 5-fluorouracil.

* * * * *